US012569217B2

(12) United States Patent
Matsuzaki et al.

(10) Patent No.: US 12,569,217 B2
(45) Date of Patent: Mar. 10, 2026

(54) X-RAY IMAGING APPARATUS AND X-RAY IMAGING METHOD

(71) Applicant: FUJIFILM Healthcare Corporation, Chiba (JP)

(72) Inventors: Kazuki Matsuzaki, Chiba (JP); Isao Takahashi, Chiba (JP); Keisuke Yamakawa, Chiba (JP); Tadashi Nakamura, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 168 days.

(21) Appl. No.: 18/418,324

(22) Filed: Jan. 21, 2024

(65) Prior Publication Data

US 2024/0245380 A1 Jul. 25, 2024

(30) Foreign Application Priority Data

Jan. 23, 2023 (JP) ................................. 2023-008113

(51) Int. Cl.
*A61B 6/58* (2024.01)
*A61B 6/00* (2006.01)
*A61B 6/40* (2024.01)

(52) U.S. Cl.
CPC ............ *A61B 6/584* (2013.01); *A61B 6/4007* (2013.01); *A61B 6/4441* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 11,571,177 B1* | 2/2023 | Douglas ................... | A61B 6/06 |
| 2014/0039303 A1* | 2/2014 | Kanzaki ............... | A61B 6/4452 |
| | | | 600/424 |

FOREIGN PATENT DOCUMENTS

| | | |
|---|---|---|
| JP | 2013173015 | 9/2013 |
| JP | 2021133036 | 9/2021 |

* cited by examiner

*Primary Examiner* — Hoon K Song
(74) *Attorney, Agent, or Firm* — JCIPRNET

(57) ABSTRACT

Provided is an X-ray imaging apparatus that has a calibration function and can understand a three-dimensional position of a treatment tool in real time during a medical operation without rotating a column of an X-ray tube.
A calibration member supported by any one of a first column, a second column, or a top plate, is disposed at a predetermined calibration position in a space irradiated with X-rays from a first X-ray tube and a second X-ray tube. A first X-ray image is acquired by irradiating a subject placed on the top plate with the X-rays from the first X-ray tube supported by the first column and detecting the X-rays transmitted through the subject by an X-ray detector disposed in the top plate. A second X-ray image is acquired by irradiating the subject with the X-rays from the second X-ray tube supported by the second column at a position shifted from an optical axis of the first X-ray tube and detecting the X-rays transmitted through the subject by the X-ray detector. A position of an image of the calibration member included in the first X-ray image and a position of an image of the calibration member included in the second X-ray image are used to calculate a three-dimensional position of the calibration member and to obtain a misregistration amount from the calibration position.

16 Claims, 11 Drawing Sheets

(a) SIDE SURFACE (b) FRONT SURFACE (b) FRONT SURFACE (a) SIDE SURFACE (a) SIDE SURFACE (b) FRONT SURFACE

FIG. 3

(a) SIDE SURFACE (b) FRONT SURFACE

FIG. 11

X-RAY IMAGE CAPTURED WITH FIRST X-RAY TUBE DURING MEDICAL OPERATION

X-RAY IMAGING APPARATUS AND X-RAY IMAGING METHOD

INCORPORATION BY REFERENCE

The present application claims priority from Japanese patent application JP-2023-008113 filed on Jan. 23, 2023, the content of which is hereby incorporated by reference into this application.

BACKGROUND OF THE INVENTION

1. Field of the Invention

The present invention relates to an X-ray imaging apparatus.

2. Description of the Related Art

A general X-ray imaging apparatus can perform X-ray imaging of a still image or X-ray imaging (so-called fluoroscopy) of a moving image by continuous imaging by irradiating a subject with X-rays from an X-ray source to detect the X-rays transmitted through the subject by a planar X-ray detector. X-ray images obtained in both the X-ray imaging and the fluoroscopy are two-dimensional projection images, and it is not possible to understand a position of a structure in the subject in a thickness direction.

Therefore, in order to enable three-dimensional imaging of the subject, for example, JP2013-173015A proposes an X-ray imaging apparatus in which a multi-X-ray generation apparatus including M×N X-ray sources and a planar detector including K×L sensors are made to face each other with an arm. This X-ray imaging apparatus can acquire any multi-layer tomographic image by periodically performing irradiation with X-rays from the plurality of X-ray sources while rotating the arm about a slide rotation axis and a main axis, and synchronously operating the sensors, imaging a plurality of multidirectional images, and performing reconstruction based on coordinate information of the X-ray sources.

In addition, JP2021-133036A discloses a so-called biplane X-ray imaging apparatus. This X-ray imaging apparatus has a configuration in which a first X-ray tube and a first X-ray detector are disposed to face each other by a first C-type arm, and a second X-ray tube and a second X-ray detector are disposed to face each other by a second C-type arm. Rotation axes of the first C-type arm and the second C-type arm are set to intersect with each other. A three-dimensional image can be obtained by rotating each of the first C-type arm and the second C-type arm to perform imaging.

SUMMARY OF THE INVENTION

The biplane X-ray imaging apparatus in the related art as in JP2021-133036A is large and expensive. On the other hand, in a multi-tube system using the M×N X-ray sources as in JP2013-173015A, it is necessary to prepare a large number of X-ray sources, the configuration is complicated, and the apparatus is large.

In addition, in order to accurately detect position coordinates of the treatment tool during a medical operation in a predetermined three-dimensional coordinate system, such as a real space coordinate system or a device coordinate system set in the device, it is necessary to dispose a predetermined phantom point at a specific point A whose position coordinates are known in advance, detect three-dimensional position coordinates of the predetermined phantom point by the X-ray imaging apparatus, and calibrate a position detection function of the X-ray imaging apparatus so that position coordinates of the point A known in advance and the three-dimensional position coordinates detected by the X-ray imaging apparatus match. However, it is not easy to obtain the position coordinates of the specific point A in advance and dispose the phantom at the position. For example, in order to detect the position of the specific point A in advance in the real space, a three-dimensional position detection device, such as optical or magnetic device, is separately required. In order to indicate the specific point A in a three-dimensional space to a user or a serviceman in the device coordinate system of the X-ray imaging apparatus, an optical device or the like indicating the specific point A which is one point in the three-dimensional space is separately required. In addition, it is not easy work to accurately perform registration and install the predetermined phantom point at the specific point A in the three-dimensional space.

An object of the present invention is to provide an X-ray imaging apparatus that has a calibration function and can understand a three-dimensional position of a treatment tool in real time during a medical operation with a minimum necessary and a compact configuration.

In order to achieve the above object, an aspect of the present invention provides an X-ray imaging apparatus including a top plate on which a subject is placed, a first X-ray tube that irradiates the subject with X-rays, a first column that supports the first X-ray tube, a second X-ray tube that irradiates the subject with X-rays, a second column that supports the second X-ray tube, an X-ray detector that detects the X-rays that are applied from the first X-ray tube and the second X-ray tube, an operation unit, and a calibration member. The second X-ray tube is disposed at a position shifted from an optical axis of the first X-ray tube by the second column. The operation unit acquires a first X-ray image from output of the X-ray detector that has detected the X-rays applied from the first X-ray tube, acquires a second X-ray image from output of the X-ray detector that has detected the X-rays applied from the second X-ray tube, and uses a position of an image of a predetermined feature part included in the first X-ray image and a position of an image of the feature part included in the second X-ray image to calculate a three-dimensional position of the predetermined feature part. The calibration member is supported by any one of the first column, the second column, or the top plate, at a predetermined calibration position in a space irradiated with the X-rays from the first X-ray tube and the second X-ray tube.

With the X-ray imaging apparatus according to the aspect of the present invention, it is possible to detect the three-dimensional position of the treatment tool in real time during the medical operation without rotating the column of the X-ray tube, and since the calibration function is provided, it is possible to easily calibrate the three-dimensional position and accurately detect the three-dimensional position.

BRIEF DESCRIPTION OF THE DRAWINGS (a) of FIG. 1 is a diagram showing a schematic configuration in a case in which a state in which a second X-ray tube 110 and a calibration member 180 of an X-ray imaging apparatus 1 according to an embodiment of the present invention are accommodated is viewed from a side surface, and (b) of FIG. 1 is a diagram showing a schematic configuration as viewed from a front surface.

(a) of FIG. 2 is a diagram showing a schematic configuration in a case in which a state in which the second X-ray tube 110 and the calibration member 180 of the X-ray imaging apparatus 1 according to the embodiment of the present invention protrude is viewed from a side surface, and (b) of FIG. 2 is a diagram showing a schematic configuration as viewed from a front surface.

(a) of FIG. 3 is a diagram showing a schematic configuration in a case in which a state in which the second X-ray tube 110 of the X-ray imaging apparatus 1 according to an embodiment of the present invention protrudes and the calibration member 180 is accommodated is viewed from a side surface, and (b) of FIG. 3 is a diagram showing a schematic configuration as viewed from a front surface.

Figure 6:
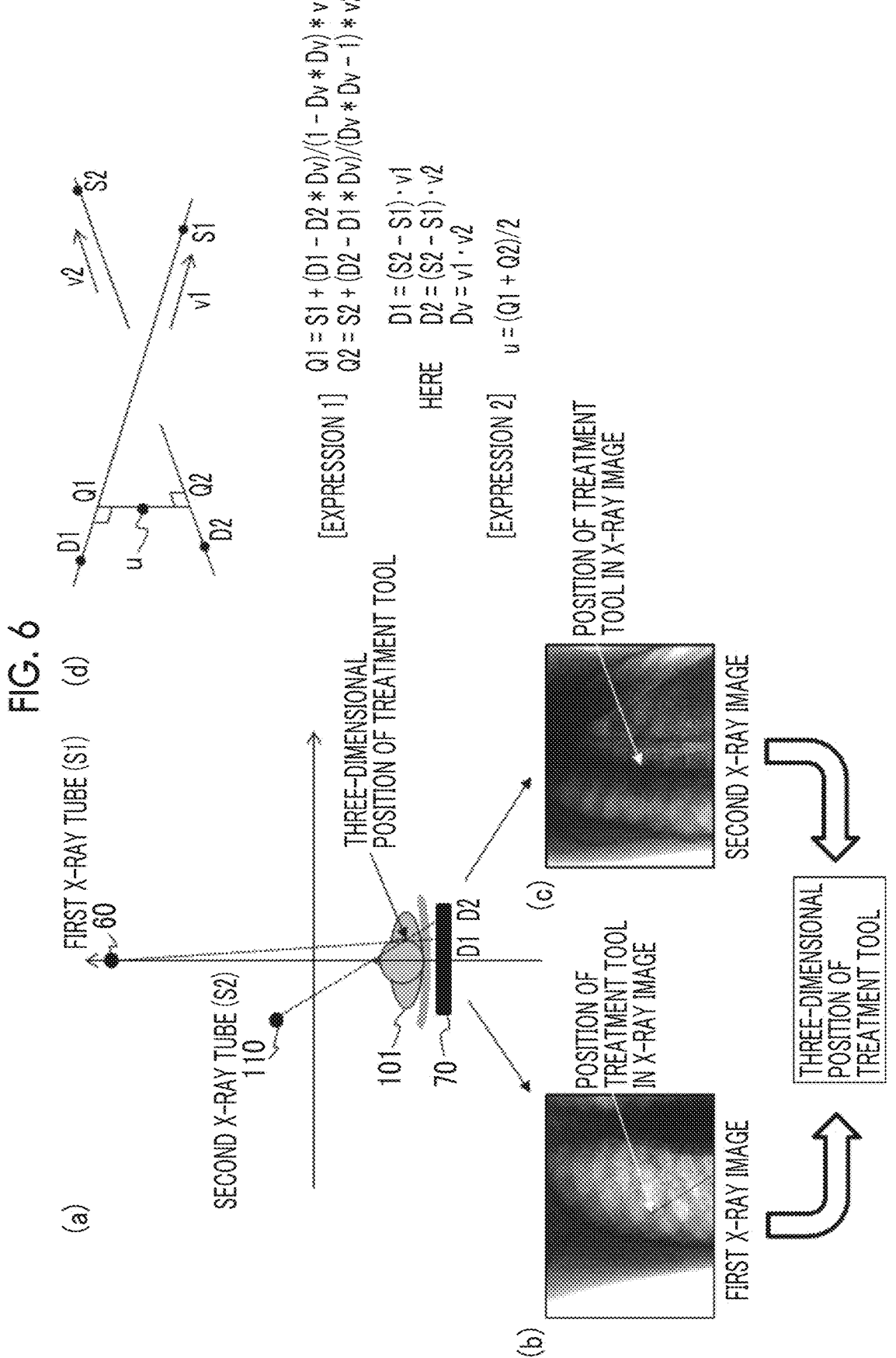

(a) of FIG. 6 is an explanatory diagram showing three-dimensional positions S1 and S2 of the first X-ray tube 60 and the second X-ray tube 110 of the X-ray imaging apparatus 1 according to the embodiment and three-dimensional positions D1 and D2 of a feature part of a treatment tool projected onto the X-ray detector 70, (b) of FIG. 6 is a diagram showing an example of a first X-ray image, (c) of FIG. 6 is a diagram showing an example of a second X-ray image, and (d) of FIG. 6 is a diagram showing a calculation method of the three-dimensional position of the feature part of the treatment tool.

Figure 7:
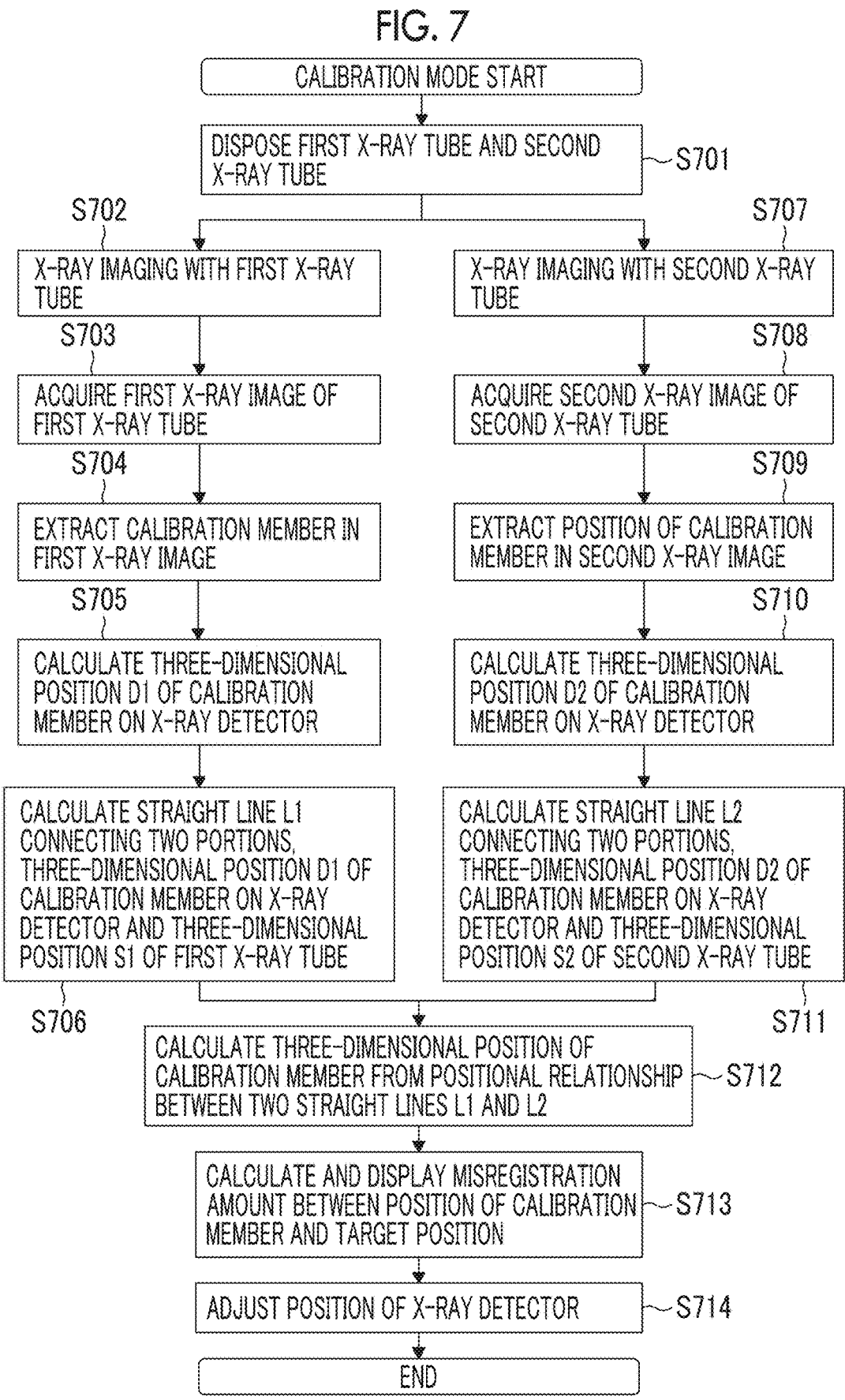

FIG. 7 is a flowchart showing an operation in a calibration mode of the X-ray imaging apparatus 1 according to the embodiment.

Figure 8:
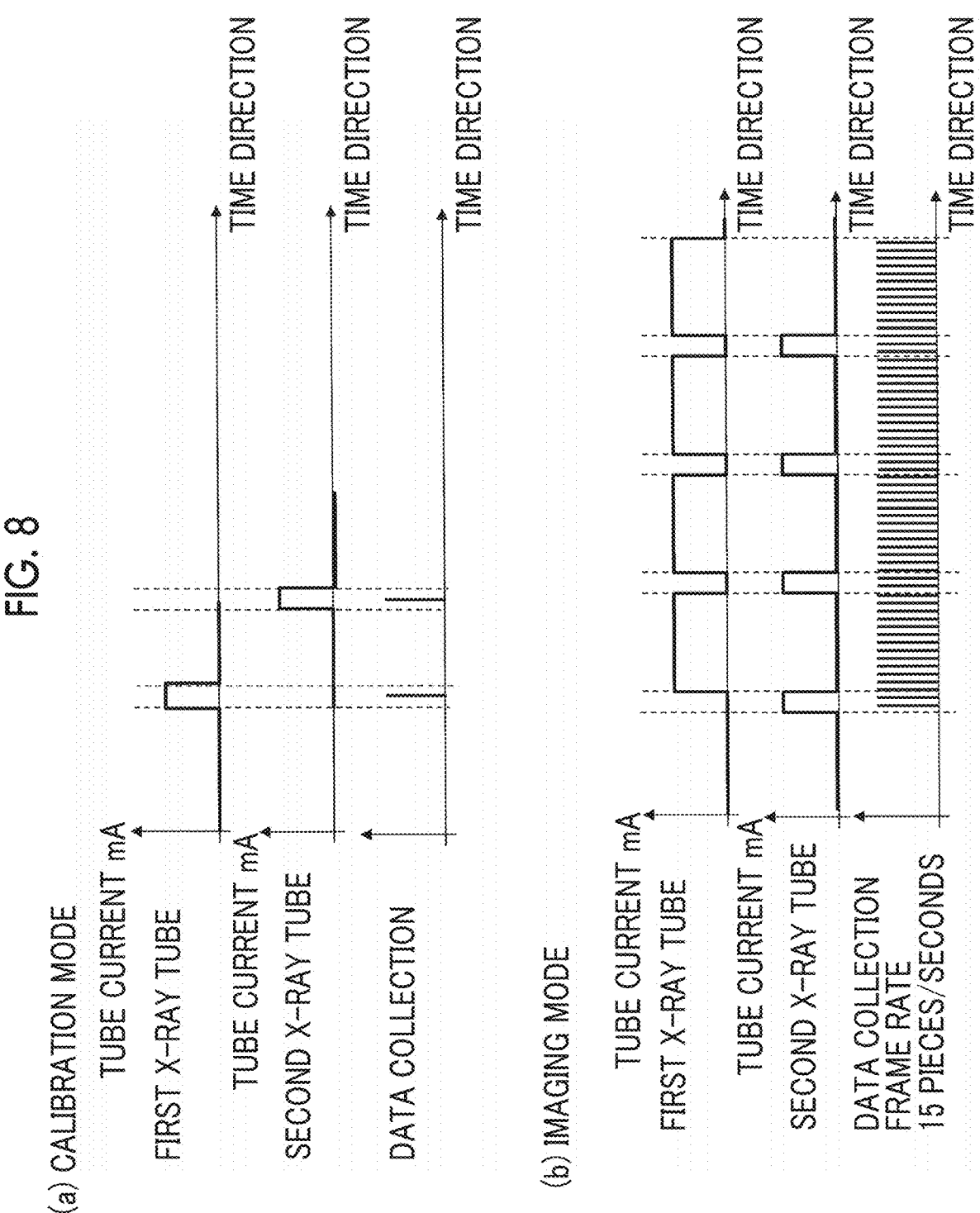

(a) of FIG. 8 is a sequence diagram showing timings of supplying a tube current of a first X-ray tube, supplying a tube current of a second X-ray tube, and data collection in the calibration mode of the X-ray imaging apparatus according to the embodiment, and (b) of FIG. 8 is a sequence diagram showing timings of supplying the tube current of a first X-ray tube, supplying the tube current of the second X-ray tube, and the data collection in the imaging mode of the X-ray imaging apparatus according to the embodiment.

Figure 9:
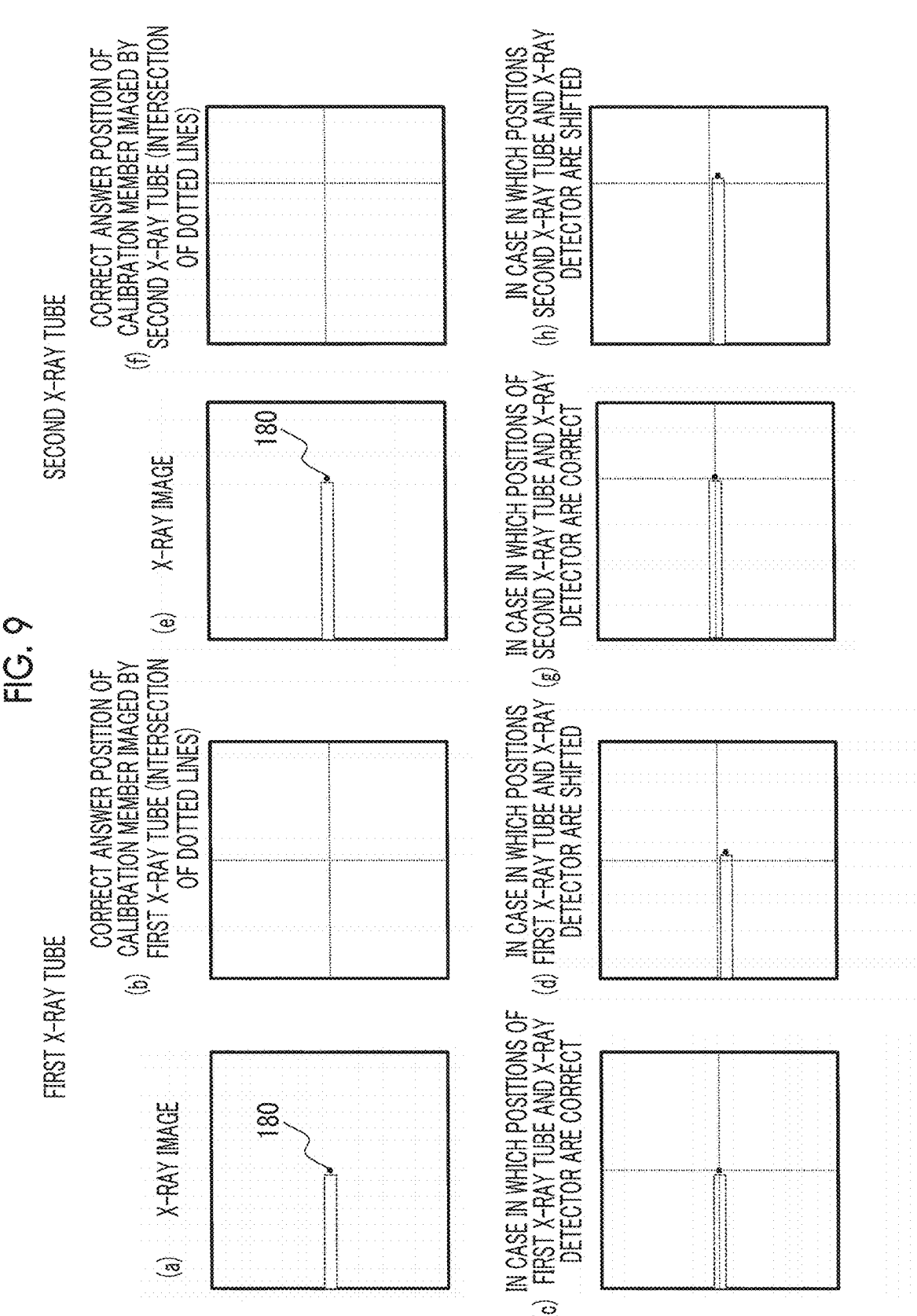

(a) to (h) of FIG. 9 are diagrams showing an example of an image captured by the X-ray imaging apparatus 1 according to Embodiment 1.

Figure 10:
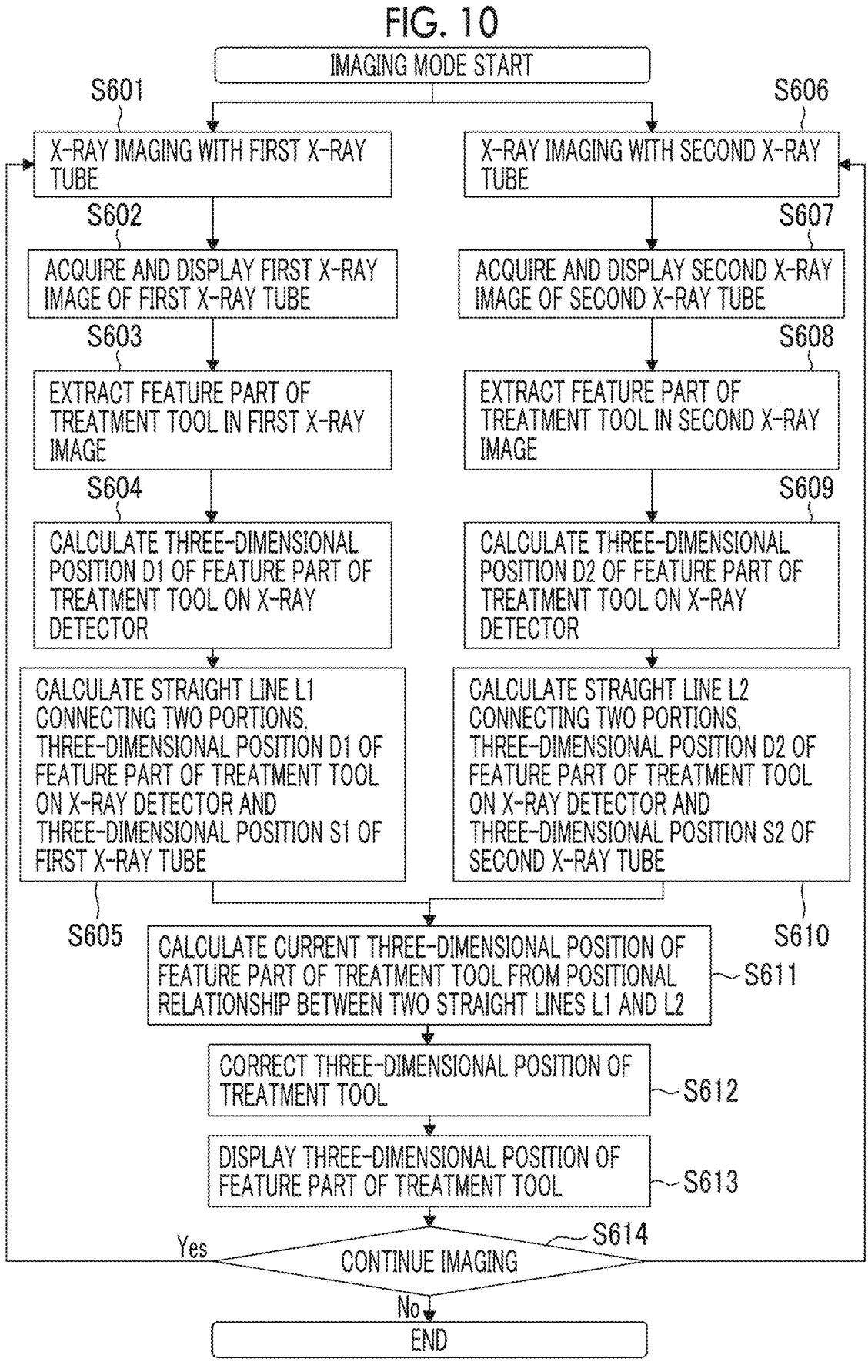

FIG. 10 is a flowchart showing an operation in the imaging mode of the X-ray imaging apparatus 1 according to the embodiment.

Figure 11:
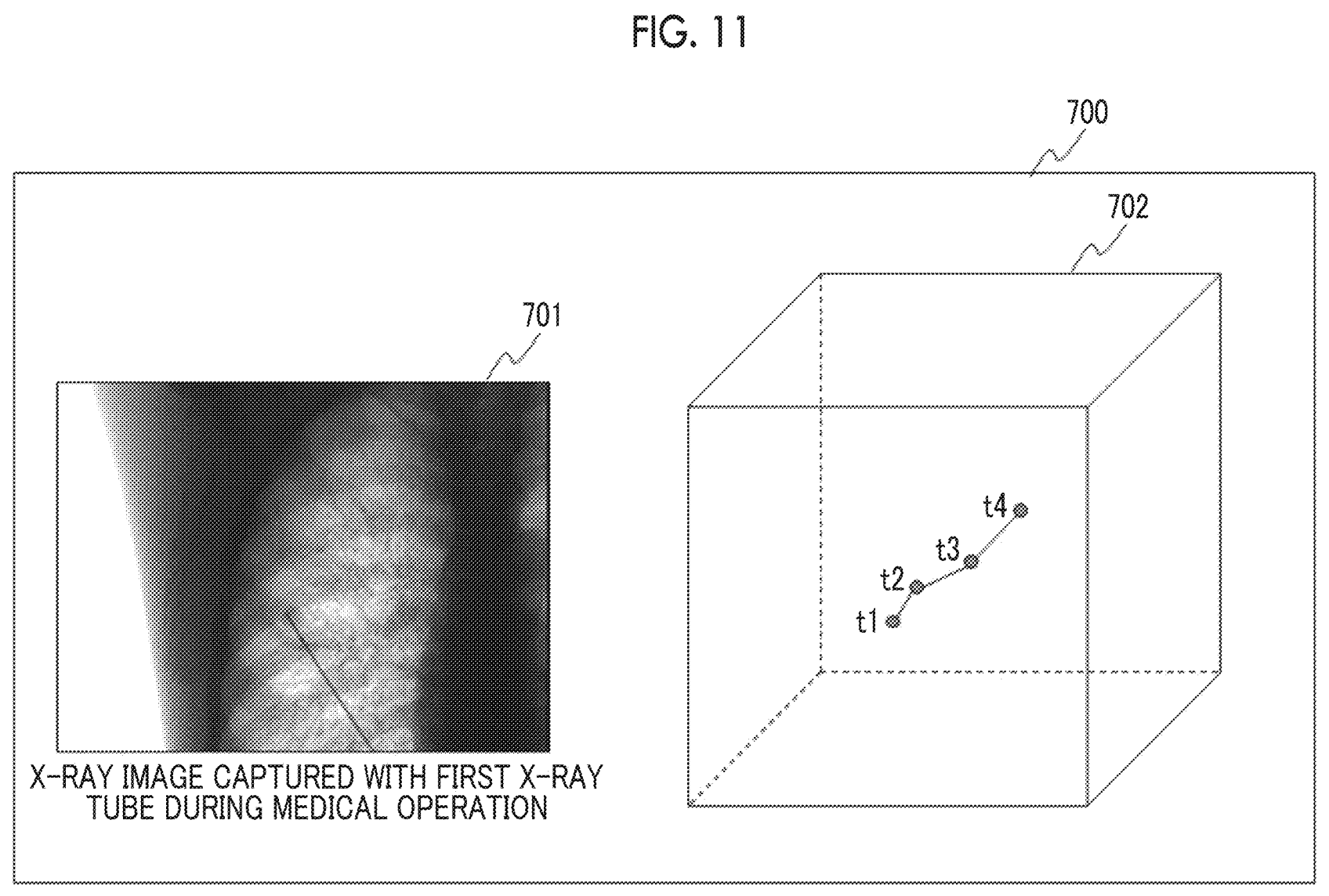

FIG. 11 is a diagram showing an example of a screen displayed on a display unit of the X-ray imaging apparatus 1 according to the embodiment.

DESCRIPTION OF THE PREFERRED EMBODIMENTS

Hereinafter, embodiments of the present invention will be described with reference to the accompanying drawings.

A configuration of an X-ray imaging apparatus 1 according to the embodiment will be described.

Figure 1:
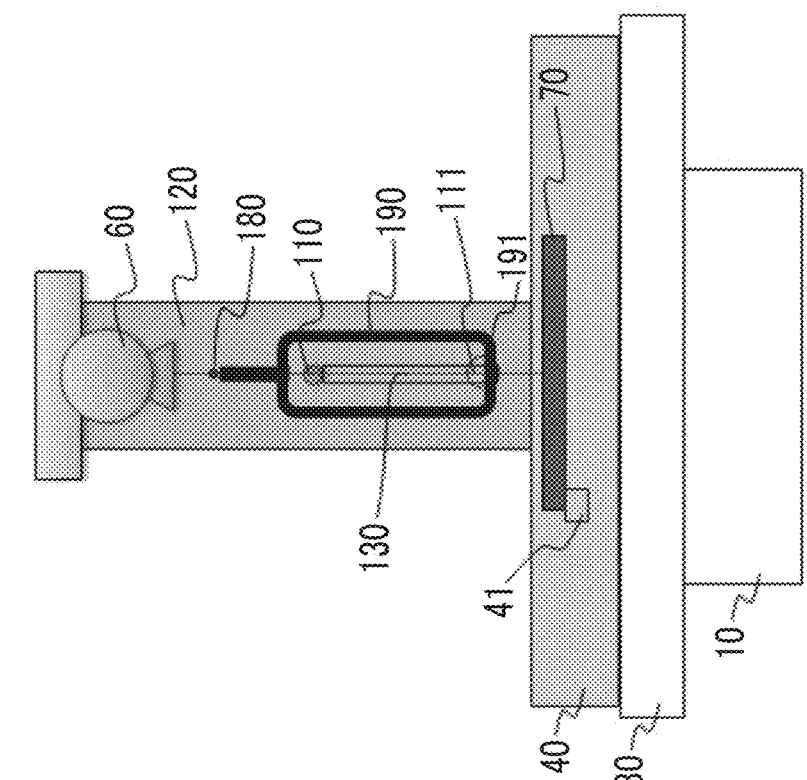
Figure 1:
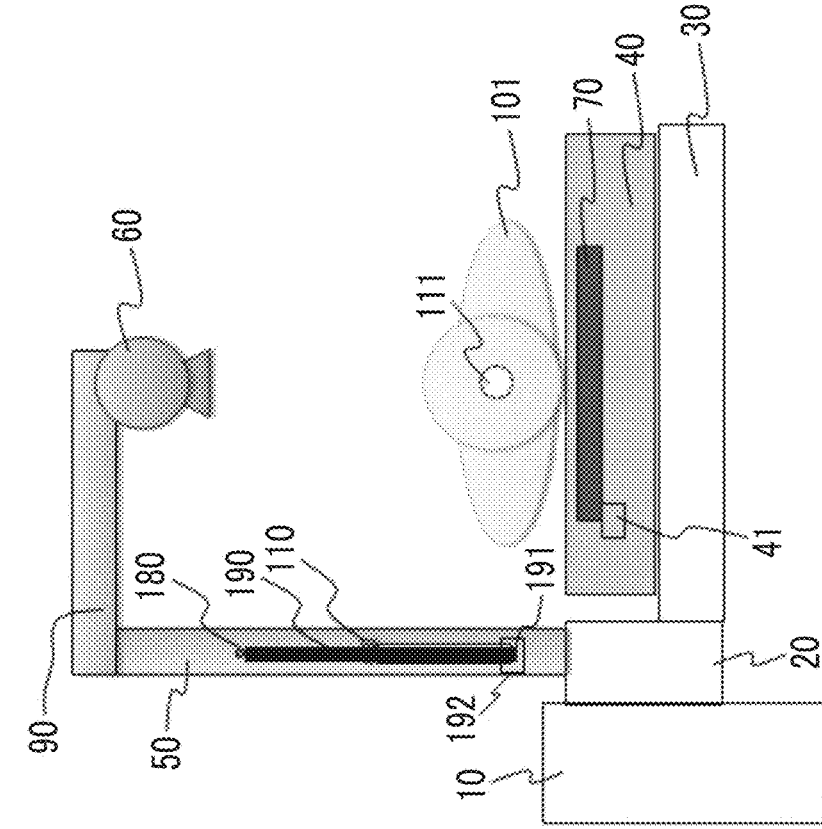
Figure 2:
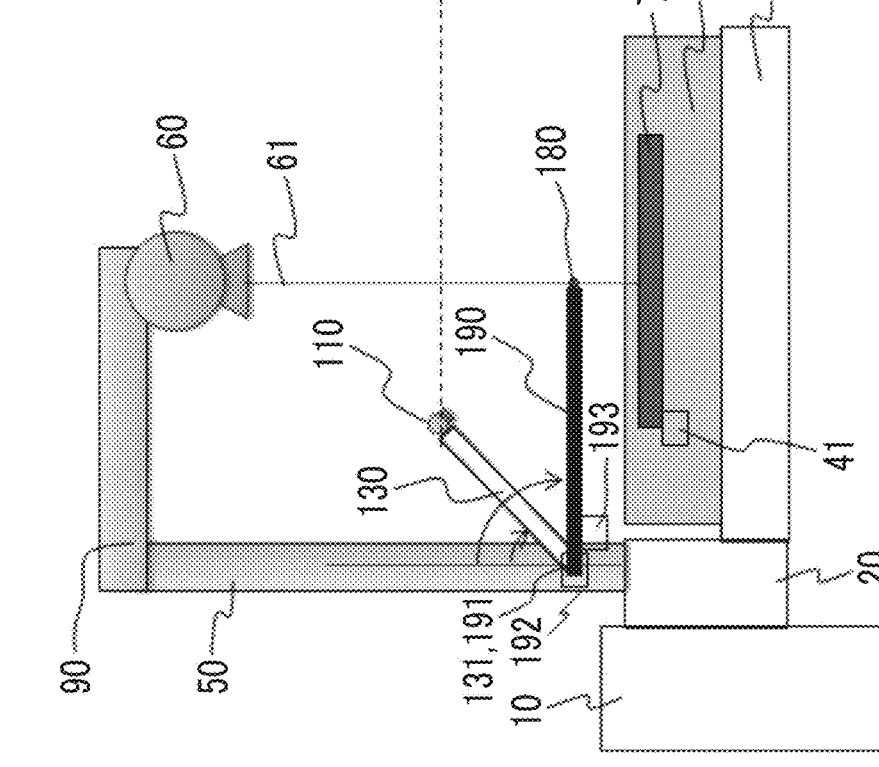
Figure 3:
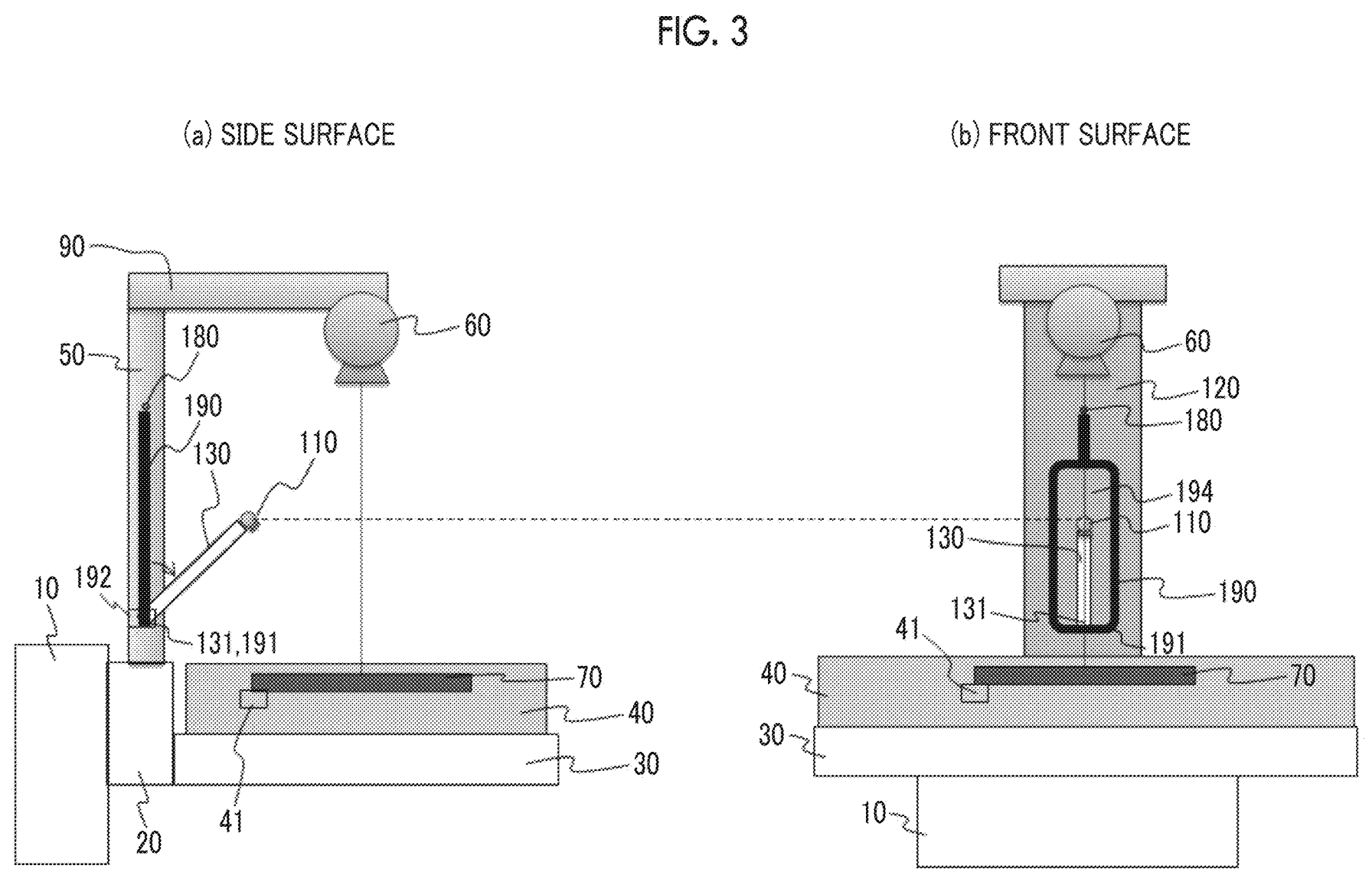
Figure 4:
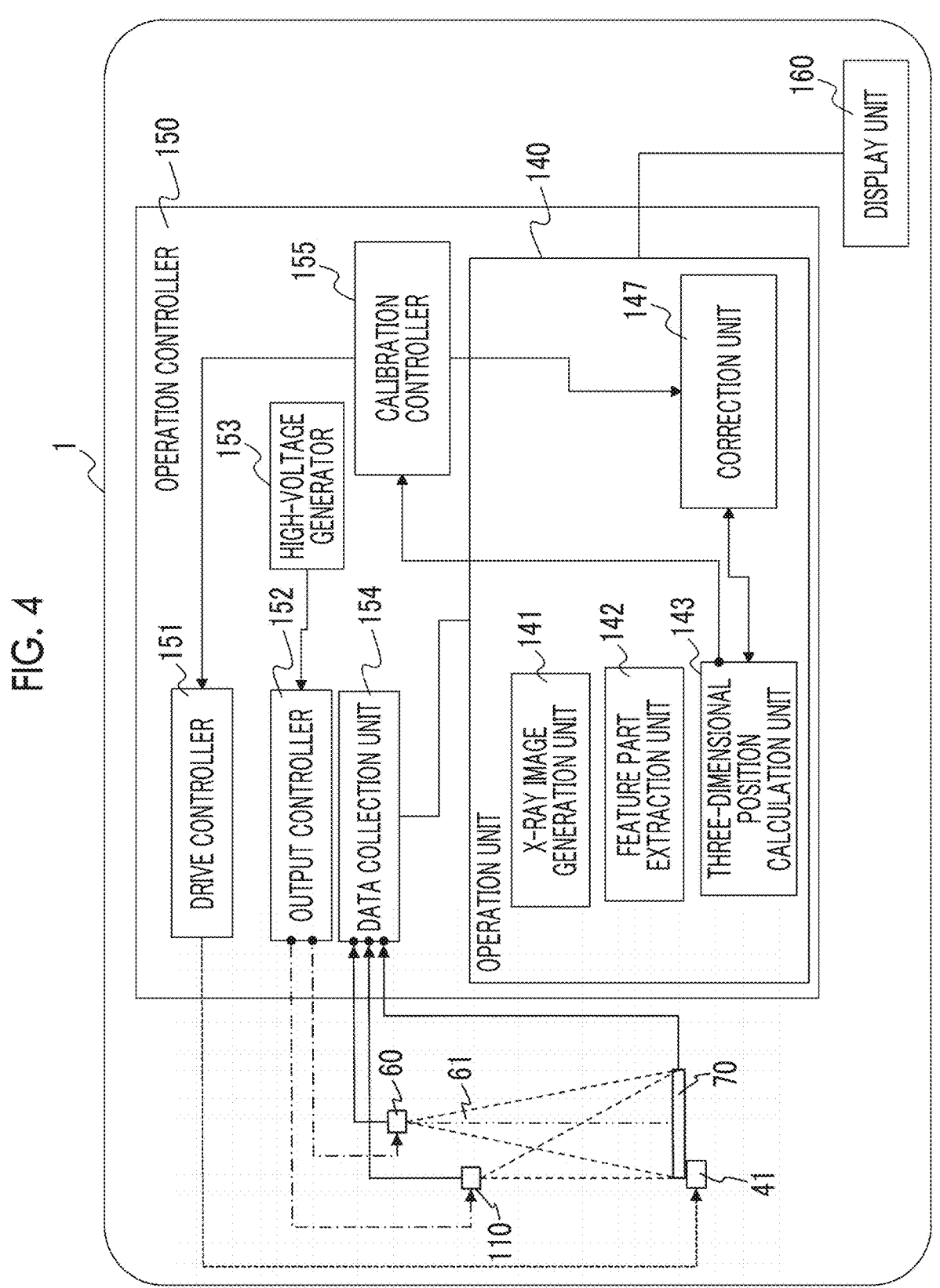
FIG. 4 is a block diagram showing a configuration of main units of the X-ray imaging apparatus 1 according to the embodiment.

FIGS. 1 to 3 are diagrams showing a schematic configuration of the X-ray imaging apparatus 1 as viewed from a side surface and a front surface, respectively. (a) and (b) of FIG. 1 show a state in which a second X-ray tube 110 and a calibration member 180 are accommodated, (a) and (b) of FIG. 2 show a state in which the second X-ray tube 110 and the calibration member 180 protrude, and (a) and (b) of FIG. 3 show a state in which the second X-ray tube 110 protrudes and the calibration member 180 is accommodated. FIG. 4 is a block diagram showing a configuration of main units of the X-ray imaging apparatus 1.

As shown in FIGS. 1 to 3, the X-ray imaging apparatus 1 comprises a top plate 40 on which a subject 101 is placed, a first X-ray tube 60, a second X-ray tube 110, a first column 50, the second column 130, an X-ray detector 70, the calibration member 180, and an operation controller 150.

The first X-ray tube 60 and the second X-ray tube 110 irradiate the subject 101 with X-rays. The first column 50 supports the first X-ray tube 60. The second column 130 supports the second X-ray tube. The X-ray detector 70 detects the X-rays that are applied from the first X-ray tube 60 and the second X-ray tube 110 and are transmitted through the subject.

The calibration member 180 is supported by any one of the first column 50, the second column 130, or the top plate 40, is supported at a predetermined calibration position 111 in a space irradiated with the X-rays from the first X-ray tube 60 and the second X-ray tube 110.

It is preferable that the calibration member 180 is supported by any one of the first column 50, the second column 130, or the top plate 40 to be able to appear and disappear. The calibration member 180 is disposed at the calibration position 111 in a protruding state, and is disposed at a position outside the space irradiated with the X-rays from the first X-ray tube 60 and the second X-ray tube 110 in a non-protruding state. As a result, only in a case in which a position detection function of the X-ray imaging apparatus 1 is calibrated, the calibration member 180 is caused to protrude and disposed at the calibration position 111 in the space irradiated with the X-rays. After the calibration ends, the calibration member 180 can be returned to a non-protruding state and accommodated not to interfere with the imaging.

As the calibration member 180, an object that absorbs the X-rays, for example, a metal sphere is used.

Here, an example will be described in which the calibration member 180 is supported by the first column 50. Specifically, the first column 50 comprises a calibration rotational movement column 190 disposed along a side surface of the first column 50. A central axis of the calibration rotational movement column 190 is parallel to a central axis of the first column 50 in a non-rotational movement state. The calibration member 180 is fixed to a distal end of the calibration rotational movement column 190. A base 191 of the calibration rotational movement column 190 is fixed to the first column 50 in a rotationally movable manner. As a result, in a case of performing the calibration, the calibration member 180 can be disposed at the calibration position 111 by causing the calibration rotational movement column 190 to move rotationally by 90° about the base 191. In addition, after the calibration ends, the calibration rotational movement column 190 can be returned to the original position, and the calibration member 180 can be accommodated in the first column 50.

A driving unit 192 such as a motor that causes the calibration rotational movement column 190 to move rotationally about the base 191 up to a predetermined angle (here, 90°) may be disposed at the first column 50, and the calibration rotational movement column 190 may be caused to move rotationally by the driving unit 192. In addition, a configuration may be adopted in which the calibration rotational movement column 190 is manually caused to move rotationally. In a case of manual rotational movement, it is desirable that a stopper 193 that stops and supports the calibration rotational movement column 190 with respect to the first column 50 at a predetermined rotational movement angle (90°) is provided (see (a) and (b) of FIG. 2).

In addition, the first column 50 comprises, as the second column 130, a second X-ray tube rotational movement column disposed along the side surface of the first column 50 (hereinafter, also referred to as a second X-ray tube rotational movement column 130) The second X-ray tube 110 is supported at a distal end of the second X-ray tube rotational movement column 130. A base 131 of the second X-ray tube rotational movement column 130 is fixed to the first column 50 in a rotationally movable manner. The second X-ray tube rotational movement column 130 moves rotationally about the base 131 of the second X-ray tube rotational movement column 130 to dispose the second X-ray tube 110 at a position for irradiating the X-ray detector 70 with the X-rays. The second X-ray tube 110 is disposed at a position shifted from an optical axis 61 of the first X-ray tube 60 by the second X-ray tube rotational movement column (second column) 130. The position shifted from the optical axis 61 of the first X-ray tube 60 means that the second X-ray tube 110 is located outside an irradiation region of the first X-ray tube 60, and also includes a case in which incidence angles of an optical axis of the second X-ray tube 110 and the optical axis 61 of the first X-ray tube 60 with respect to the subject 101 are different from each other.

In addition, a relative position of the second X-ray tube 110 with respect to the first X-ray tube 60 can be changed by changing the rotational movement angle of the second X-ray tube rotational movement column 130.

A configuration can be adopted in which one of the calibration rotational movement column 190 or the second X-ray tube rotational movement column 130 is provided with an opening 194 along the central axis, and the other is disposed in the opening 194. With such a configuration, it is possible to match the central axes of both the calibration rotational movement column 190 and the second X-ray tube rotational movement column 130 in a state in which the calibration rotational movement column 190 and the second X-ray tube rotational movement column 130 are in a non-rotational movement state. This configuration is preferable because the second X-ray tube 110 and the calibration member 180 can be disposed on the central axes of the calibration rotational movement column 190 and the second X-ray tube rotational movement column 130.

Here, as shown in (b) of FIG. 1, the calibration rotational movement column 190 is provided with an opening 194 along the central axis, and the second column 130 is disposed in the opening 194.

A driving unit such as a motor that causes the second X-ray tube rotational movement column 130 to move rotationally about the base 131 up to a predetermined angle (for example, 45°) may be disposed in the first column 50, and the second X-ray tube rotational movement column 130 may be caused to move rotationally by the driving unit. In addition, a configuration may be adopted in which the second X-ray tube rotational movement column 130 is manually caused to move rotationally. In a case of manual rotational movement, it is desirable that a stopper that stops and supports the second X-ray tube rotational movement column 130 with respect to the first column 50 at a predetermined rotational movement angle (for example, 45°) is provided.

In addition, a configuration may be adopted in which a central axis of rotational movement of the base 191 of the calibration rotational movement column 190 match a central axis of rotational movement of the base 131 of the second X-ray tube rotational movement column 130. In a case in which the central axis of the rotational movement of the base 191 of the calibration rotational movement column 190 and the central axis of the rotational movement of the base 131 of the second X-ray tube rotational movement column 130 match, as the driving unit that causes the second X-ray tube rotational movement column 130 to move rotationally or the stopper that stops the second X-ray tube rotational movement column 130, the driving unit 192 or the stopper 193 of the calibration rotational movement column 190 can be used in combination.

Figure 5:
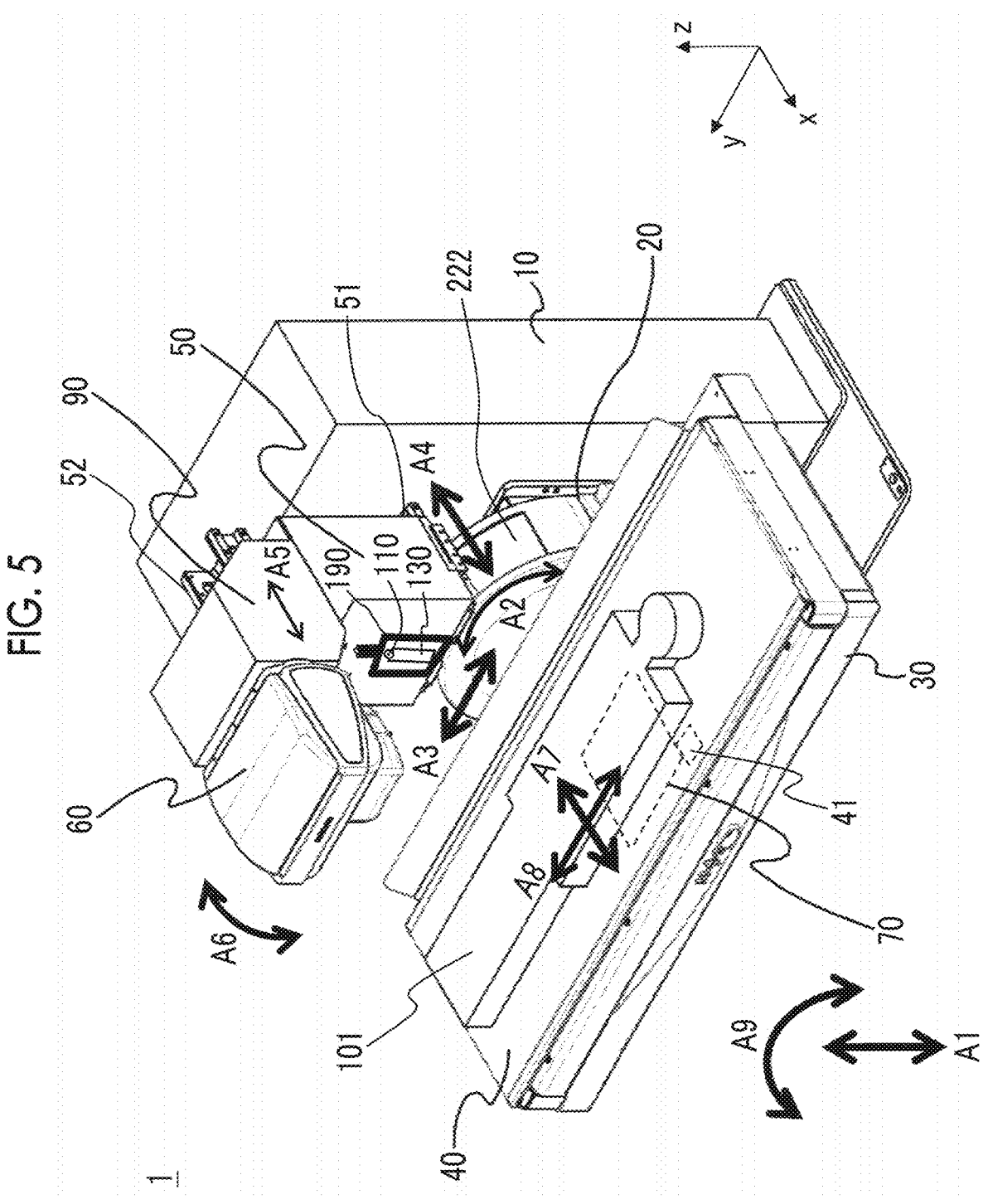
FIG. 5 is a perspective view of the X-ray imaging apparatus 1 according to the embodiment.

The configuration of other portions of the X-ray imaging apparatus 1 will be further described with reference to FIGS. 1 to 3, and 5. FIG. 5 is a perspective view of the X-ray imaging apparatus 1.

The first X-ray tube 60 is attached to a distal end of the first X-ray support arm 90 supported on an upper end of the first column 50. A lower end of the first column 50 is supported with respect to the column support arm 20 provided on the stand 10.

A position at which the second X-ray tube 110 is disposed by the second X-ray tube rotational movement column (second column) 130 in a case of the irradiation with the X-rays is a position that is shifted from an optical axis 61 of the first X-ray tube 60 and is closer to the subject 101 than the first X-ray tube 60.

In addition, a maximum irradiation region of the X-rays from the second X-ray tube 110 to the X-ray detector 70 may be smaller than a maximum irradiation region of the X-rays from the first X-ray tube 60 to the X-ray detector 70.

Maximum output of the X-rays of the second X-ray tube 110 may be smaller than maximum output of the X-rays of the first X-ray tube 60.

In addition, the first X-ray support arm 90 that supports the first X-ray tube 60 comprises a second slide mechanism 52 that moves a position of the first X-ray tube 60 in the width direction (A5 direction=x direction) of the top plate 40 with respect to the first column 50. Further, a first rotation mechanism that causes the first X-ray tube 60 to move rotationally (in A6 direction) about an axis parallel to the major axis (y axis) of the top plate 40 at a distal end of the first X-ray support arm 90 is disposed at a connecting portion between the first X-ray tube 60 and the first X-ray support arm 90.

In addition, a first slide mechanism 51 that moves a lower end of the first column 50 in the width direction (f direction=x direction) of the top plate 40 with respect to the stand 10 is provided between the lower end of the first column 50 and the column support arm 20. As a result, the first column 50 and the second column 130 can be integrally moved in the x direction.

A support frame 30 that supports the top plate 40 is mounted on the column support arm 20 in addition to the first column 50. The stand 10 has a built-in drive mechanism (not shown) that moves the column support arm 20 up and down (A1 direction=z axis). As a result, the top plate 40 and the first X-ray tube 60 can be moved up and down while maintaining the positional relationship between the first X-ray tube 60 and the top plate 40.

In addition, the column support arm 20 of the stand 10 has a built-in moving mechanism (not shown) that moves the first column 50 in the major axis direction (A3 direction=y axis) of the top plate 40. As a result, the first X-ray tube 60 and the second X-ray tube 110 can be moved with respect to the top plate 40 in the major axis direction (y axis) of the top plate 40.

In addition, the stand 10 comprises a raising and lowering mechanism (not shown) that rotates the column support arm 20 (in A9 direction) with the central axis (x axis) of the column support arm 20 as a rotation center. As a result, the top plate 40 can be moved up and down while maintaining the positional relationship between the first X-ray tube 60 and the top plate 40.

Further, a connecting portion between the column support arm 20 and the first column 50 comprises an inclination mechanism 222 that causes the first column 50 to move rotationally (in A2 direction) with the central axis (x axis) of the column support arm 20 as a rotation center with respect to the column support arm 20 along a semi-circular rail. As a result, the first column 50 can be inclined with respect to the top plate 40 with the x axis as a rotation center.

Further, an X-ray detector drive mechanism 41 that moves the X-ray detector 70 in the major axis direction (A8 direction) and a minor axis direction (A7 direction) of the top plate 40 with respect to the top plate 40 is provided in the top plate 40.

The above-described drive mechanism, such as the first slide mechanism 51 or the X-ray detector drive mechanism 41, may have any configuration. As an example, a configuration can be adopted in which a rack disposed along the movement direction, a pinion that meshes with the rack, and a motor that rotates the pinion are provided.

The operation controller 150 comprises a calibration controller 155, a drive controller 151, an output controller 152, a high-voltage generator 153, a data collection unit 154, and an operation unit 140. The drive controller 151 controls the operations of the driving unit 192 such as a motor that causes the calibration rotational movement column 190 and the second X-ray tube rotational movement column 130 to move rotationally, and each drive mechanism, such as the first slide mechanism 51 or the X-ray detector drive mechanism 41.

The output controller 152 supplies a high-voltage generated by the high-voltage generator 153 to the first X-ray tube 60 and the second X-ray tube 110 with set voltage value and current value, respectively, and applies the X-rays from the first X-ray tube 60 and the second X-ray tube 110. The output controller 152 can individually control the output of the first X-ray tube 60 and the output of the second X-ray tube 110.

The data collection unit 154 collects signals output by X-ray detection elements two-dimensionally arranged in the X-ray detector 70 in response to the irradiation with the X-rays. In addition, the data collection unit 154 acquires information on the start and end of the irradiation from each X-ray tube from the tube current and the tube voltage that are controlled by the output controller 152.

The operation unit 140 comprises an X-ray image generation unit 141, a feature part extraction unit 142, a three-dimensional position calculation unit 143, and a correction unit 147.

The X-ray image generation unit 141 receives the output of the X-ray detector 70 that has detected the X-rays applied from the first X-ray tube, from the data collection unit 154, to generate a first X-ray image (see (b) of FIG. 5). In addition, the X-ray image generation unit 141 receives the output of the X-ray detector 70 that has detected the X-rays applied from the second X-ray tube, from the data collection unit 154, to generate a second X-ray image (see (c) of FIG. 5).

The feature part extraction unit 142 extracts a position of an image of a predetermined feature part included in the first X-ray image and a position of an image of the feature part included in the second X-ray image by a known method. An intraoperative feature part is, for example, a distal end of a treatment tool, such as a catheter. The feature part in a case of the calibration is the calibration member 180.

The three-dimensional position calculation unit 143 uses the position of the image of the predetermined feature part included in the first X-ray image and the position of the image of the feature part included in the second X-ray image calculate a three-dimensional position of the image of the predetermined feature part.

An example of a specific calculation method of the feature part will be described. As shown in (a) of FIG. 6, a three-dimensional position (real space coordinates) of the first X-ray tube 60 is denoted by S1, a three-dimensional position (real space coordinates) of the feature part in the first X-ray image is denoted by D1, and a straight line connecting S1 and D1 is denoted by L1. In addition, a three-dimensional position of the second X-ray tube 110 is denoted by S2, a three-dimensional position of the feature part in the second X-ray image is denoted by D2, and a straight line connecting S2 and D2 is denoted by L2. The same feature part such as the distal end of the treatment tool are projected onto D1 and D2. Therefore, the straight lines L1 and L2 ideally intersect with each other at one point as shown in (a) of FIG. 6. Actually, as shown in (d) of FIG. 6, there are cases where the straight lines L1 and L2 do not intersect with each other due to a measurement error or the like. Therefore, a point Q1 on the straight line S1-D1 and a point Q2 on the straight line S2-D2 where the distance between the two straight lines is closest are obtained, and for example, a midpoint u of the two points can be set as the position of the image of the feature part.

The points Q1 and Q2 shown in (c) of FIG. 6 can be obtained according to Expression 1.

$$Q1 = S1 + (D1 - D2 * Dv)/(1 - Dv * Dv) * v1 \qquad (1)$$

$$Q2 = S2 + (D2 - D1 * Dv)/(Dv * Dv - 1) * v2$$

$$\text{Here,}$$

$$D1 = (S2 - S1) \, v1$$

$$D2 = (S2 - S1) \, v2$$

$$Dv = v1 \cdot v2$$

From the three-dimensional positions of the points Q1 and Q2 obtained by Expression 1, the three-dimensional position u of the feature part can be calculated by using Expression 2.

$$u = (Q1 + Q2)/2 \qquad (2)$$

Calibration Mode

The operations of the calibration controller 155 and the correction unit 147 will be described with reference to FIG. 7, (a) of FIG. 8, and (a) to (h) of FIG. 9.

FIG. 7 is a flowchart showing an operation in a calibration mode constituting the coordinate system of the X-ray imaging apparatus 1. (a) of FIG. 8 is a timing chart showing an X-ray irradiation timings of the first X-ray tube 60 and the second X-ray tube 110 and a data collection timing of the X-ray detector 70 in the calibration mode. (a) to (h) of FIG. 9 show examples of an image.

Step S701

In a case in which the operator gives an instruction to start the calibration mode, the calibration controller 155 drives the driving unit 192 to cause the calibration rotational movement column 190 to move rotationally by 90°, and to cause the second X-ray tube rotational movement column 130 to move rotationally by a predetermined angle (for example, 45°). As a result, the calibration rotational movement column 190 is disposed at the predetermined calibration position 111. In addition, the calibration controller 155 controls each drive mechanism to dispose the first X-ray tube 60 and the second X-ray tube 110 at the predetermined calibration positions, respectively.

Step S702

As shown in (a) of FIG. 8, first, the output controller 152 supplies the tube current and the tube voltage, which are set by the operator, to the first X-ray tube 60, irradiates the subject 101 with the X-rays from the first X-ray tube 60, and performs the X-ray imaging.

Step S703

The X-ray image generation unit 141 collects X-ray data detected by the X-ray detector 70 by the data collection unit 154. As a result, the X-ray image generation unit 141 receives the output of the X-ray detector 70 from the data collection unit 154, to generate the first X-ray image (see (a) of FIG. 9).

Step S704

The feature part extraction unit 142 performs image processing on the first X-ray image generated in step S703 to extract the calibration member 180 in the first X-ray image.

Step S705

The three-dimensional position calculation unit 143 calculates the three-dimensional position D1 on the X-ray detector 70 onto which the calibration member 180 is projected, based on the position of the calibration member 180 in the first X-ray image.

Step S706

The three-dimensional position calculation unit 143 calculates the straight line L1 connecting the two points, the three-dimensional position D1 of the calibration member 180 on the X-ray detector 70 and the three-dimensional position S1 of the first X-ray tube 60.

Step S707

Next, as shown in (a) of FIG. 8 the output controller 152 supplies the tube current and the tube voltage, which are set by the operator, to the second X-ray tube 110, irradiates the subject 101 with the X-rays from the second X-ray tube 110, and performs the X-ray imaging.

Step S708

The X-ray image generation unit 141 collects the X-ray data detected by the X-ray detector 70 by the data collection unit 154. As a result, the X-ray image generation unit 141 receives the output of the X-ray detector 70 from the data collection unit 154, to generate the second X-ray image (see (e) of FIG. 9).

Step S709

The feature part extraction unit 142 performs image processing on the second X-ray image generated in step S708 to extract the calibration member 180 in the second X-ray image.

Step S710

The three-dimensional position calculation unit 143 calculates the three-dimensional position D2 on the X-ray detector 70 onto which the calibration member 180 is projected, based on the position of the calibration member 180 in the second X-ray image.

Step S711

The three-dimensional position calculation unit 143 calculates the straight line L2 connecting the two points, the three-dimensional position D2 of the calibration member 180 on the X-ray detector 70 and the three-dimensional position S2 of the second X-ray tube 110.

Step S712

The three-dimensional position calculation unit 143 calculates the three-dimensional position coordinates of the calibration member 180 from a positional relationship between the two straight lines L1 and L2 by using Expressions 1 and 2.

Step S713

The calibration controller 155 calculates a difference (misregistration amount) between the position coordinates of the calibration member 180 calculated in step S712 and the position coordinates of the known calibration position 111. The calibration controller 155 displays, on the display unit 160, an image in which the misregistration amount can be understood.

As an example of a display screen, the first X-ray image (see (a) of FIG. 9) and the second X-ray image (see (c) of FIG. 9) generated in steps S703 and S708, respectively, and images (for example, see (b) and (f) of FIG. 9) showing the positions of the known calibration position 111 on the first X-ray image and on the second X-ray image with marks, respectively, can be overlapped and displayed.

As a result, in a case in which the position coordinates of the calibration member 180 and the position coordinates of the known calibration positions 111 match, the positions of the images of the calibration member 180 in the first X-ray image and the second X-ray image, and a mark (here, cross mark) for a calibration position are overlapped and displayed (see (c) and (g) of FIG. 9). On the other hand, in a case in which the position coordinates of the calibration member 180 are shifted from the position coordinates of the known calibration positions 111, the positions of the images of the calibration member 180 in the first X-ray image and the second X-ray image, and a mark for a calibration position are shifted and displayed (see (d) and (h) of FIG. 9). As a result, a user who views the display unit 160 can easily understand the misregistration amount.

Step S714

The calibration controller 155 calculates the movement direction and the movement amount of the position of the X-ray detector 70 in the principal plane of the top plate 40 by using a predetermined mathematical expression, table, or the like in accordance with the misregistration amount and the misregistration direction so that the misregistration amount calculated in step S714 is canceled. The calibration controller 155 instructs the X-ray detector drive mechanism 41 to move the X-ray detector 70 by the calculated movement amount in the calculated movement direction.

The X-ray detector drive mechanism 41 adjusts the position of the X-ray detector 70 in accordance with the instruction, and performs the calibration.

As described above, by executing the calibration mode, the X-ray imaging apparatus 1 can automatically dispose the calibration member 180 at the predetermined calibration position 111, detect the three-dimensional position of the calibration member 180, detect the misregistration amount from the three-dimensional position coordinates of the calibration position 111, and automatically perform the calibration for canceling the misregistration amount. Therefore, it is possible to easily calibrate the three-dimensional position detected by the X-ray imaging apparatus 1, and it is possible to accurately detect the three-dimensional position coordinates of the feature part to be detected in the imaging mode.

In the flow of FIG. 7, the position of the X-ray detector 70 is adjusted by the X-ray detector drive mechanism 41 in step S714, but the calibration method is not limited to this method.

For example, instead of adjusting the position of the X-ray detector 70 in step S714, the misregistration amount calculated in step S713 may be used to create a correction table for correcting the misregistration of the feature part detected in the imaging mode. Alternatively, an appropriate correction table may be selected from a plurality of types of correction tables obtained in advance in accordance with the calculated misregistration amount.

In addition, in step S714, the user may manually adjust the position of the X-ray detector 70 instead of the X-ray detector drive mechanism 41.

Imaging Mode

Next, the operation of each unit of the X-ray imaging apparatus 1 in the imaging mode will be described with reference to (a) to (d) of FIG. 6, (b) of FIG. 8, and FIG. 10. Here, the operation in the imaging mode in a case in which the correction table is generated in step S714 during the execution of the calibration mode will be described.

(a) to (d) of FIG. 6 are diagrams showing an operation of calculating the three-dimensional position. (b) of FIG. 8 is a timing chart showing the X-ray irradiation timings of the first X-ray tube 60 and the second X-ray tube 110 and the data collection timing of the X-ray detector 70 in the imaging mode. FIG. 10 is a flowchart showing the operation in the imaging mode.

The X-ray imaging apparatus 1 performs the imaging with the second X-ray tube 110 at a predetermined timing while performing the fluoroscopy with the first X-ray tube 60 during the medical operation, and can understand the three-dimensional position of the feature part of the treatment tool in real time. In this case, since it is not necessary to rotate the X-ray tube and the X-ray detector, the operator does not need to move back, and the operator does not need to stop performing the procedure, such as inserting the treatment tool.

Step S601

In a case in which the operator gives an instruction to start the imaging, the subject 101 is irradiated with the X-rays from the first X-ray tube 60 to start X-ray imaging.

Specifically, the drive controller 151 controls the operation of each of the drive mechanisms in accordance with the instruction of the operator, to dispose the first X-ray tube 60 at the position desired by the operator. The output controller 152 supplies the tube current and the tube voltage, which are set by the operator, to the first X-ray tube 60 for a predetermined time, and performs the irradiation with the X-rays.

Step S602

The X-ray image generation unit 141 acquires an X-ray image from the X-rays applied from the first X-ray tube 60.

Specifically, the X-rays that are applied from the first X-ray tube 60 and are transmitted through the subject 101 are detected by the X-ray detector 70, and the output of the X-ray detector 70 is collected by the data collection unit 154 at a predetermined frame rate as shown in (b) of FIG. 8.

The X-ray image generation unit 141 receives the output of the X-ray detector 70 from the data collection unit 154, to generate the first X-ray image (see (b) of FIG. 6). The X-ray image generation unit 141 displays the first X-ray image on the display unit 160, as shown in (b) of FIG. 6.

The operator inserts the treatment tool (catheter or the like) into the subject 101 while viewing the first X-ray image on the display unit 160.

Step S603

The feature part extraction unit 142 performs image processing on the first X-ray image generated in step S602 to extract the feature part (for example, the distal end of the treatment tool) of the treatment tool in the first X-ray image.

Step S604

The three-dimensional position calculation unit 143 calculates the three-dimensional position D1 (real space coordinates) on the X-ray detector 70 onto which the feature part of the treatment tool is projected, based on the position of the treatment tool in the first X-ray image (see (a) of FIG. 6).

Step S605

The three-dimensional position calculation unit 143 calculates the straight line L1 connecting the two points, the three-dimensional position D1 (real space coordinates) of the feature part of the treatment tool on the X-ray detector and the three-dimensional position S1 (real space coordinates) of the first X-ray tube 60.

Step S606

At a timing at which the irradiation with the X-rays from the first X-ray tube 60 ends, as shown in (b) of FIG. 8, the subject 101 is irradiated with the X-rays from the second X-ray tube 110 to perform the X-ray imaging.

Specifically, the drive controller 151 controls the operation of each of the drive mechanisms 121 to 123 in accordance with the instruction of the operator, to dispose the second X-ray tube 110 at the position desired by the operator. The output controller 152 supplies the tube current and the tube voltage, which are set by the operator, to the second X-ray tube 110 for a predetermined time, and performs the irradiation with the X-rays.

Step S607

The X-ray image generation unit 141 acquires an X-ray image from the X-rays applied from the second X-ray tube 110.

Specifically, the X-rays that are applied from the second X-ray tube 110 and are transmitted through the subject 101 are detected by the X-ray detector 70, and the output of the X-ray detector 70 is collected by the data collection unit 154.

The X-ray image generation unit 141 receives the output of the X-ray detector 70 from the data collection unit 154, to generate the second X-ray image (see (c) of FIG. 6).

As a result, the operator can check the second X-ray image captured from an angle different from an angle of the first X-ray image on the display unit 160.

Step S608

The feature part extraction unit 142 performs image processing on the second X-ray image generated in step S607 to extract the feature part (the distal end of the treatment tool) of the treatment tool in the second X-ray image.

Step S609

The three-dimensional position calculation unit 143 calculates the three-dimensional position D2 (real space coordinates) on the X-ray detector 70 onto which the feature part of the treatment tool is projected, based on the position of the treatment tool in the second X-ray image.

Step S610

The three-dimensional position calculation unit 143 calculates the straight line L2 connecting the two points, the three-dimensional position D2 (real space coordinates) of the feature part of the treatment tool on the X-ray detector and the three-dimensional position S2 (real space coordinates) of the second X-ray tube 110.

Step S611

The three-dimensional position calculation unit 143 calculates the three-dimensional position coordinates of the feature part of the treatment tool from a positional relationship between the two straight lines L1 and L2 by using Expressions 1 and 2 (see (d) of FIG. 6).

Step S612

The correction unit 147 receives the correction table from the calibration controller 155, obtains a correction amount for correcting the three-dimensional position coordinates of the feature part of the treatment tool calculated in step S611 based on the correction table, and corrects the three-dimensional position coordinates by adding the correction amount.

Step S613

The three-dimensional position calculation unit 143 displays, on the display unit 160, the three-dimensional position of the feature part of the treatment tool after the correction by the correction unit 147 side by side with a first X-ray image 701, for example, as shown in the screen example of FIG. 11. The operator can understand a projection image of the subject 101 and the treatment tool from the first X-ray image 701, and can understand a temporal change of a depth of the distal end of the treatment tool from the three-dimensional image 702.

Step S614

An instruction to continue the imaging from the operator is checked, and in a case in which the imaging is to be continued, the process returns to step S601, the imaging with the first X-ray tube 60 is continued, the imaging with the second X-ray tube 110 of steps S606 to S610 is performed at regular time intervals as shown in (b) of FIG. 8, the position of the feature part of the treatment tool is calculated, and the display is updated. As a result, the positions of the feature part of the treatment tool are acquired in time series at regular time intervals.

As described above, according to the present embodiment, since the imaging can be performed by the second X-ray tube 110 while the imaging is performed by the first X-ray tube 60 during the medical operation, the three-dimensional position of the feature part of the treatment tool can be detected in real time. Moreover, since the three-dimensional position of the feature part of the treatment tool can be corrected based on the correction table generated in the calibration mode by the calibration controller 155 in step S612, the detection accuracy of the three-dimensional position of the feature part can be improved.

In the flow of FIG. 10, the three-dimensional position of the feature part of the treatment tool is corrected based on the correction table generated in the calibration mode in step S612, but in a case in which the position of the X-ray detector 70 is already adjusted in step S714 of FIG. 7 in the calibration mode, it is not necessary to correct the three-dimensional position of the feature part in the imaging mode. In this case, step S612 of the flow of FIG. 6 is not executed.

Since the position of the second X-ray tube 110 with respect to the subject 101 and the irradiation direction with respect to the subject 101 can be relatively adjusted by the drive mechanism, the X-rays can be applied to the feature part of the treatment tool even in a case in which the irradiation range is narrowed, and the detection accuracy of the position of the feature part of the treatment tool is improved.

In addition, since the distance between the second X-ray tube 110 and the X-ray detector 70 can be adjusted by the rotational movement angle, the second X-ray tube 110 can be brought closer to the subject 101, and a small X-ray tube having small output and a narrow irradiation range can be used as the second X-ray tube 110. As a result, the second X-ray tube 110 does not interfere with the imaging with the first X-ray tube 60, and the first X-ray tube 60 and the second X-ray tube 110 can perform the imaging in parallel in real time.

In a case in which the positions of the images of the feature part acquired in time series in step S611 are moved, in a case in which step S606 is subsequently executed, it is desirable that the drive controller 151 operates at least one of the plurality of drive mechanisms or the driving unit 192 to change at least one of the position, the distance, or the X-ray irradiation direction of the second X-ray tube 110 with respect to the subject 101, and causes the irradiation region of the X-rays from the second X-ray tube 110 with respect to the subject 101 to track the movement of the positions of the feature part. By performing the tracking in this manner, even in a case in which the irradiation region of the X-rays from the second X-ray tube 110 is small, it is possible to always include the moving feature part in the irradiation region.

EXPLANATION OF REFERENCES

1: X-ray imaging apparatus
10: stand
20: column support arm
30: support frame
40: top plate
41: X-ray detector drive mechanism
50: first column
52: second slide mechanism
60: first X-ray tube
61: optical axis
70: X-ray detector
90: first X-ray support arm
101: subject
110: second X-ray tube
111: calibration position
130: second column (second X-ray tube rotational movement column)
131: base
140: operation unit
141: X-ray image generation unit
142: feature part extraction unit
143: three-dimensional position calculation unit
144: three-dimensional image acquisition unit
145: two-dimensional projection image creation unit
146: image registration unit
147: correction unit
150: operation controller
151: drive controller
152: output controller
153: high-voltage generator
154: data collection unit
155 calibration controller
160: display unit
180: calibration member
190: calibration rotational movement column
191: base
192: driving unit
193: stopper
194: opening
222: inclination mechanism
701: first X-ray image
702: three-dimensional image

What is claimed is:

1. An X-ray imaging apparatus comprising:
a top plate on which a subject is placed;
a first X-ray tube that irradiates the subject with X-rays;
a first column that supports the first X-ray tube;
a second X-ray tube that irradiates the subject with X-rays;
a second column that supports the second X-ray tube;
an X-ray detector that detects the X-rays that are applied from the first X-ray tube and the second X-ray tube;
an operation unit; and
a calibration member,
wherein the second X-ray tube is disposed at a position shifted from an optical axis of the first X-ray tube by the second column,
the operation unit acquires a first X-ray image from output of the X-ray detector that has detected the X-rays applied from the first X-ray tube, acquires a second X-ray image from output of the X-ray detector that has detected the X-rays applied from the second X-ray tube, and uses a position of an image of a predetermined feature part included in the first X-ray image and a position of an image of the feature part included in the second X-ray image to calculate a three-dimensional position of the predetermined feature part, and
the calibration member is supported by any one of the first column, the second column, or the top plate, at a predetermined calibration position in a space irradiated with the X-rays from the first X-ray tube and the second X-ray tube,
wherein the calibration member is supported by any one of the first column, the second column, or the top plate to be able to appear and disappear, is disposed at the calibration position in a protruding state, and is disposed at a position outside the space irradiated with the X-rays from the first X-ray tube and the second X-ray tube in a non-protruding state.

2. The X-ray imaging apparatus according to claim 1, wherein the calibration member is an object that absorbs the X-rays,
the first column includes a calibration rotational movement column disposed along a side surface of the first column, and
the calibration member is fixed to a distal end of the calibration rotational movement column, a base of the calibration rotational movement column is fixed to the first column in a rotationally movable manner, and the calibration rotational movement column moves rotationally about the base to dispose the calibration member at the calibration position.

3. The X-ray imaging apparatus according to claim 2, wherein the first column is provided with a driving unit that causes the calibration rotational movement column to move rotationally about the base up to a predetermined angle.

4. The X-ray imaging apparatus according to claim 2, wherein the first column is provided with a stopper that stops and supports the calibration rotational movement column with respect to the first column at a predetermined rotational movement angle.

5. The X-ray imaging apparatus according to claim 2, wherein a central axis of the calibration rotational movement column in a non-rotational movement state is parallel to a central axis of the first column.

6. The X-ray imaging apparatus according to claim 2, wherein the first column includes a second X-ray tube rotational movement column disposed along the side surface of the first column, and
the second X-ray tube is supported at a distal end of the second X-ray tube rotational movement column, a base of the second X-ray tube rotational movement column is fixed to the first column in a rotationally movable manner, and the second X-ray tube rotational movement column moves rotationally about the base of the second X-ray tube rotational movement column to dispose the second X-ray tube at a position for irradiating the X-ray detector with the X-rays.

7. The X-ray imaging apparatus according to claim 6, wherein one of the calibration rotational movement column or the second X-ray tube rotational movement column is provided with an opening along a central axis, and the other is disposed in the opening, and
in a state in which both the calibration rotational movement column and the second X-ray tube rotational movement column do not move rotationally, the central axes of the calibration rotational movement column and the second X-ray tube rotational movement column match.

8. The X-ray imaging apparatus according to claim 7, wherein a central axis of rotational movement of the base of the calibration rotational movement column and a central axis of rotational movement of the base of the second X-ray tube rotational movement column match.

9. The X-ray imaging apparatus according to claim 6, wherein the first column is provided with a driving unit for a second X-ray tube that causes the second X-ray tube rotational movement column to move rotationally about the base of the second X-ray tube rotational movement column up to a predetermined angle.

10. The X-ray imaging apparatus according to claim 6, wherein the first column is provided with a stopper for a second X-ray tube that stops and supports the second X-ray tube rotational movement column with respect to the first column at a predetermined rotational movement angle.

11. The X-ray imaging apparatus according to claim 1, further comprising:
a calibration controller; and
an X-ray detector driving unit that moves a position of the X-ray detector in a principal plane of the top plate,
wherein the calibration controller disposes the calibration member at the calibration position, calculates a position of the calibration member by the operation unit, obtains a misregistration amount of the calculated position of the calibration member from a predetermined position, and shifts the position of the X-ray detector by the X-ray detector driving unit in accordance with the obtained misregistration amount.

12. The X-ray imaging apparatus according to claim 1, further comprising:
a calibration controller; and
a correction unit that corrects the three-dimensional position of the feature part calculated by the operation unit,
wherein the calibration controller disposes the calibration member at the calibration position, calculates a position of the calibration member by the operation unit, and obtains a misregistration amount of the calculated position of the calibration member from a predetermined position, and
the correction unit corrects the three-dimensional position of the feature part calculated by the operation unit, in accordance with the obtained misregistration amount.

13. The X-ray imaging apparatus according to claim 1, wherein a maximum irradiation region of the X-rays from the second X-ray tube to the X-ray detector is smaller than a maximum irradiation region of the X-rays from the first X-ray tube to the X-ray detector.

14. The X-ray imaging apparatus according to claim 1, wherein maximum output of the X-rays from the second X-ray tube is smaller than maximum output of the X-rays from the first X-ray tube.

15. The X-ray imaging apparatus according to claim 14, further comprising:

an output controller that controls output of the first X-ray tube and output of the second X-ray tube, wherein the output controller is configured to individually control the output of the first X-ray tube and the output of the second X-ray tube.

16. An X-ray imaging method comprising:

disposing a calibration member supported by any one of a first column, a second column, or a top plate, at a predetermined calibration position in a space irradiated with X-rays from a first X-ray tube and a second X-ray tube;

acquiring a first X-ray image by irradiating the space with the X-rays from the first X-ray tube supported by the first column and detecting the X-rays transmitted through the space by an X-ray detector;

acquiring a second X-ray image by irradiating the space with the X-rays from the second X-ray tube supported by the second column at a position shifted from an optical axis of the first X-ray tube and detecting the X-rays transmitted through the space by the X-ray detector; and using a position of an image of the calibration member included in the first X-ray image and a position of an image of the calibration member included in the second X-ray image to calculate a three-dimensional position of the calibration member and to obtain a misregistration amount from the calibration position, wherein the calibration member is supported by any one of the first column, the second column, or the top plate to be able to appear and disappear, is disposed at the calibration position in a protruding state, and is disposed at a position outside the space irradiated with the X-rays from the first X-ray tube and the second X-ray tube in a non-protruding state.

\* \* \* \* \*